United States Patent
Jule et al.

(10) Patent No.: US 12,315,154 B2
(45) Date of Patent: May 27, 2025

(54) SYSTEM AND METHOD FOR GENERATING AN INDICATOR FROM AN IMAGE OF A HISTOLOGICAL SECTION

(71) Applicant: Biocellvia, Marseilles (FR)

(72) Inventors: Yvon Jule, Marseilles (FR); Florent Tomi, Marseilles (FR); Damien Barbes, Marseilles (FR); Karine Bertotti, Lancon-Provence (FR)

(73) Assignee: Biocellvia, Marseilles (FR)

( * ) Notice: Subject to any disclaimer, the term of this patent is extended or adjusted under 35 U.S.C. 154(b) by 432 days.

(21) Appl. No.: 17/907,035

(22) PCT Filed: Mar. 24, 2020

(86) PCT No.: PCT/FR2020/000065
§ 371 (c)(1),
(2) Date: Sep. 22, 2022

(87) PCT Pub. No.: WO2021/191509
PCT Pub. Date: Sep. 30, 2021

(65) Prior Publication Data
US 2023/0117179 A1     Apr. 20, 2023

(51) Int. Cl.
*G06K 9/00*        (2022.01)
*C12N 5/071*      (2010.01)
(Continued)

(52) U.S. Cl.
CPC .......... *G06T 7/0012* (2013.01); *C12N 5/0671* (2013.01); *G01N 1/30* (2013.01);
(Continued)

(58) Field of Classification Search
CPC .. A61P 1/16; A61P 43/00; A61P 13/12; A61P 35/00; A61P 11/00; A61P 17/00;
(Continued)

(56) References Cited

U.S. PATENT DOCUMENTS

2015/0339816 A1*  11/2015  Yu .............................. G06T 7/10
                                                                 382/128
2017/0215814 A1    8/2017  Cales
(Continued)

FOREIGN PATENT DOCUMENTS

WO       2019077108 A2     4/2019

OTHER PUBLICATIONS

Yu, Y., Wang, J., Ng, C.W. et al. Deep learning enables automated scoring of liver fibrosis stages. Sci Rep 8, 16016, 2018 (Year: 2018).*

(Continued)

*Primary Examiner* — Alex Kok S Liew
(74) *Attorney, Agent, or Firm* — BUCHANAN, INGERSOLL & ROONEY PC (57) ABSTRACT

The invention relates to a method for producing variables of interest relating to human or animal hepatic tissue from a digital representation of a histological section. Such a method is intended to be implemented by a unit for processing a medical imaging system to automatically and quickly provide diagnosis assistance, in particular for NASH, to healthcare personnel. The variables of interest respectively describe a level of steatosis of the hepatic tissue, a level of fibrosis in the portal, central and perisinusoidal areas of the hepatic lobule and a level of inflammation of the hepatic tissue. A method according to the invention further provides for producing a multiparametric indicator in the form of graphical representations arranged to be displayed by an output human-machine interface of the medical imaging system.

12 Claims, 2 Drawing Sheets

(51) Int. Cl.
  *G01N 1/30* (2006.01)
  *G06T 7/00* (2017.01)
(52) U.S. Cl.
  CPC  *C12N 2533/54* (2013.01); *G06T 2207/10056* (2013.01); *G06T 2207/30024* (2013.01); *G06T 2207/30056* (2013.01)
(58) Field of Classification Search
  CPC ...... A61P 1/18; A61P 17/02; C12Q 2600/158; C12Q 1/6883; C12Q 1/6886; C12Q 2600/118; C12Q 1/52; C12Q 2600/112; C12Q 2600/156; G06T 2207/30024; G06T 2207/30056; G06T 7/0012; G06T 2200/24; G06T 2207/10024; G06T 2207/10056; G06T 2207/10072; A61B 5/0064; A61B 5/0077; A61B 5/444; A61B 5/7239; G16H 20/10; G16H 50/20
  See application file for complete search history.

(56) References Cited

U.S. PATENT DOCUMENTS

| | | |
|---|---|---|
| 2018/0075600 A1 | 3/2018 | Cales et al. |
| 2021/0192722 A1* | 6/2021 | Brozek ................. G16H 50/20 |
| 2024/0193785 A1* | 6/2024 | Hasegawa ............. G06V 10/82 |

OTHER PUBLICATIONS

Rudder et al., "Automated Computerized Image Analysis for the User-Independent Evaluation of Disease Severity in Preclinical Models of Nafld/Nash", Laboratory Investigation (2020), United States and Canadian Academy of Pathology, vol. 100, No. 1, Sep. 10, 2019, pp. 147-160, XP03696648.

International Search Report (PCT/ISA/210) with English translation and Written Opinion (PCT/ISA/237) mailed on Oct. 22, 2020, by the European Patent Office as the International Searching Authority for International Application No. PCT/FR2020/000065.

\* cited by examiner

SYSTEM AND METHOD FOR GENERATING AN INDICATOR FROM AN IMAGE OF A HISTOLOGICAL SECTION

The invention relates to a system and a method for generating an indicator with reference to the structural remodelling of a tissue of a human or animal organ and/or the accumulation of lipid vacuoles in said organ. Such an indicator is automatically determined based on an image, or more generally a digital representation, of a histological section of an organ, and provides an objective and reproducible aid to all healthcare personnel, so that the latter can establish an accurate diagnosis with reference to a possible human or animal pathology. Moreover, the invention provides that such an indicator can procure an objective and reproducible aid to an investigator in the laboratory, such that the latter can make a decision without ambiguity on the curative relevance of a given treatment with respect to such a pathology.

Biological imaging is currently one of the major resources in examination of the organs and the different organic tissues. In particular, it is predominantly involved in the fields of medical diagnosis support and preclinical and clinical research.

Different techniques are currently utilized in preclinical and clinical imaging, such as, non-limitatively, magnetic resonance imaging, optical, electronic, and confocal microscopy, microtomography, ultrasound scanning, CT scanning. These techniques can be utilized for in vivo or ex vivo observations. The digital images thus obtained make it possible, in the context of institutional or industrial research laboratories, more particularly to analyze a biological state of organic tissues and to assess certain beneficial and/or toxic effects of certain substances with a view to the selection thereof for the development of future medicinal products.

In the era of digital transformation, the development of such digital imaging technologies has opened new perspectives for histological analysis as a whole. The ability to access digital images or representations of histological sections has made it possible to develop new methods based on descriptive and quantitative analysis of the digital images of said histological sections, by means of computerized tools implementing algorithms or innovative procedures allowing a considerable advance in terms of precision, reliability, speed, and reproducibility.

However, utilization of the computerized tools that are currently available does not make it possible to automate the quantitative assessment of certain pathologies, such as, by way of non-limitative example, hepatic disorders. In fact, the investigator still remains only too present in the process of implementation of this assessment. Their manual intervention leads to wide variations in the characterization of the components of the samples of histological sections assessed.

Within the context of aid in the diagnosis of certain pathologies affecting the organs of the visceral region, more particularly the liver, such as, for example, the pathologies associated with hepatic steatosis, better known by the abbreviation "NAFLD" for "non-alcoholic fatty liver disease", and more commonly called "fatty liver disease", it would be particularly advantageous to be able to determine any morphological change in the hepatic tissue. NAFLD is characterized by an accumulation of lipid vesicles within the cytoplasm of the hepatic cells. However, it is currently difficult for health care personnel to determine with certainty the degree of development of NAFLD in a patient solely on the biological criteria from non-invasive clinical imaging (tomography, ultrasound, elastography, CT scanner). Ex-vivo histological analysis (biopsy and explant) remains the gold standard for establishing with certainty the diagnosis of NAFLD, as well as its severity.

Such an accumulation, generally benign, can develop in severity and at an advanced stage, result in the emergence of inflammatory processes triggered by endogenous or infiltrated pro-inflammatory immunocytes. Establishment of the inflammatory processes characterizes the passage from NAFLD to a non-alcoholic hepatic steatosis, more commonly known by the acronym "NASH" for "non-alcoholic steato-hepatitis". Inflammation of the hepatic tissue is accompanied by swelling or "ballooning" of a part of the hepatic cells. This key structural change in the hepatic cells falls within the characterization of NASH. Swelling of the hepatic cells corresponds to a lesion of the hepatic cells which inevitably leads to their necrosis. The inflammation of the hepatic tissue also leads to the formation of scar tissue, resulting in the development of fibrosis. In an advanced stage of development, NASH can develop in severity towards cirrhosis or even hepatocellular carcinoma.

The prevalence rate of NAFLD, and therefore potentially of NASH, observed in the world population as a whole is constantly increasing. At an early stage in the development of NASH, clinical and biological investigations do not allow it to be distinguished with certainty from NAFLD. The development of methods for diagnosis of these pathologies is becoming a public health challenge.

Only histological analysis of the hepatic tissue makes it possible to diagnose without ambiguity the presence of NASH and its severity. Assessment of this histological analysis is based principally on a subjective assessment method by scores, known as semi-quantitative method, covering steatosis, ballooning, inflammation, and fibrosis.

Steatosis, lesion of the liver corresponding to a lipid overload in the cytoplasm of the hepatic cells, is assessed by optical microscopy in several fields of observation or regions of interest, of histological sections stained with hematoxylin and eosin. A score having an integer value comprised between "0" and "3" is given by specialized health care personnel. This score, manually assessed, is directly linked to the percentage of hepatic cells with lipid vacuoles situated within said fields of observation. By way of example, a score equal to "0" indicates that the percentage of hepatic cells with lipid vacuoles is less than five percent of the total population of the hepatic cells located within the field of observation. A score equal to "1" corresponds to such a percentage comprised between five and thirty-three percent, a score equal to "2" to a percentage comprised between thirty-three and sixty-six percent, and a score equal to "3" to a percentage greater than sixty-six percent.

Quantification of the "ballooned" hepatic cells is assessed manually via fields of observation by specialized health care personnel on the same histological sections stained with hematoxylin and eosin that were previously used for assessment of steatosis. A score having an integer value comprised between "0" and "2" is assigned. Such a score adopts the value "0" in the absence of ballooned cells, the value "1" in the presence of several ballooned cells, the value "2" if numerous cells appear ballooned. This assessment by score of the ballooned cells does not take into account their location in the hepatic lobule.

Hepatic fibrosis is assessed based on the level of expression of the collagen fibres the neosynthesis of which is induced by the emergence of inflammatory processes. It is estimated by scores with respect to certain determined zones of the hepatic lobule: the portal zone, the central zone and the perisinusoidal zone. The latter corresponds to an intermediate zone between the portal zone and the central zone. Such an estimation is generated based on histological sections stained with Masson's trichrome or with picrosirius red, also known by the abbreviation PSR. The preparation of a histological section based on one or more stains and/or immunolabelling is known as "staining". It consists of a step that will be referred to hereinafter for the sake of simplicity as "staining step" of the histological section. Such a preparation makes it possible to enhance one or other component or cell within the hepatic tissue. Hepatic fibrosis is assessed manually via fields of observation by specialized health care personnel, using a score having an integer value comprised between "0" and "4". A score equal to "0" indicates an absence of collagen fibres. A score equal to "1" indicates the presence of collagen fibres in the perisinusoidal or portal zone. A score equal to "2" indicates the presence of collagen fibres in both the perisinusoidal and portal zones. A score equal to "3" indicates the existence of connections or "bridging" of the collagen fibres between the different zones of the hepatic lobule. Finally, a score equal to "4" is associated with a severe fibrotic state, evidencing the presence of cirrhosis.

Hepatic inflammation is currently assessed on the basis of a manual quantification and by fields of observation of the number of immunocyte foci, groups of immunocytes greater than five immunocytes, that are inflammatory, observed per field of observation on histological sections stained with hematoxylin and eosin. This quantification of the foci is assessed subjectively by specialized health care personnel, using a score having an integer value comprised between "0" and "3". A score equal to "0" corresponds to an absence of foci, a score equal to "1" to a number of foci less than two, a score equal to "2" to a number of foci comprised between two and four and a score equal to "3" to a number of foci greater than four. These scores are assigned independently of the location of the foci within the hepatic lobule.

All the semi-quantitative data expressed by scores, such as described above, are obtained based on visual observations using optical microscopy. These observations are carried out over several fields of observation, called regions of interest, covering only a limited part of the histological section. Thus, pronounced heterogeneity with respect to the distribution of abnormalities associated with a pathology can cause false interpretations with regard to establishing a diagnosis. In order to overcome these errors of interpretation, an investigator must diversify and multiply the fields of observation so as to cover a maximum surface area of observation within the histological section.

Other techniques, called non-invasive, rely on the use of biochemical markers, within the context of blood tests, said markers generally being directed against one or more specific proteins that may be overexpressed by the hepatic cells in the case of NASH. However, these biochemical markers are very often insufficiently specific to NASH to allow a reliable diagnosis. Other non-invasive methodological approaches are used, such as ultrasound transient elastography better known as "Fibroscan" (registered trademark) for the identification of fibrosis by measurement of the elasticity of the hepatic tissue. However, these non-invasive techniques only give access to partial data on the presence of NASH, which overall does not allow the specialized health care personnel to establish an accurate, reliable, and reproducible diagnosis. Histopathological analysis therefore remains today the only method for establishing with certainty the presence and level of severity of NASH.

The non-invasive measurement methods described above are however currently very widely used, in particular for clinical investigations. Although they do not allow an accurate diagnosis of NASH to be reached, they are an aid to decision-making by specialized health care personnel in the selection of patients in whom the presence of NASH is strongly suspected and who will require a liver biopsy. It should be noted however that the non-invasive methods can have some drawbacks. Indeed, they generally require a lengthy implementation time, i.e., sometimes several hours, and are most often dependent on several investigators. This is the case in particular with Fibroscan. This may cause significant variation in obtaining data, and consequently cause inconsistent, or even contradictory, poorly reproducible diagnosis on the part of the specialized health care personnel.

Some studies based on an automated analysis of an image resulting from digitization of a histological section show the superiority of this type of analysis with respect to the manual techniques, in terms of precision and reproducibility. There may be mentioned in this respect the document "Quantification of liver fat: a comprehensive review", E. Goceri et al.—2016, which mentions briefly, without describing them, the existence of techniques for automatic quantification of steatosis based on histological data, regretting that this type of analysis has not become routine rather than visual and conventional analyses by human experts. The article "Automated image analysis method for detecting and quantifying macrovesicular steatosis in hematoxylin and eosin-stained histology images of human livers", Nativ et al.—2014 can also be mentioned, which focuses on estimating steatosis, again confirming the superiority of a digital analysis rather than a conventional method. The same applies for the article "Automatic classification of white regions in liver biopsies by supervised machine learning", Vanderbeck et al.—2014, which mentions the contribution of machine learning technology to identifying certain zones of a determined specific colour (white, in this case) based on an image of a histological section, for estimating a degree of steatosis of a hepatic tissue. Such a technique is intended to be reproducible in comparison with conventional human analyses. It should be noted however that the supervised learning required by this type of solution necessitates a high level of investment and by its nature reproduces human bias. Other studies, such as those disclosed by the document WO 2019/077108A2, attempt to extend the operation of this technology in order to distinguish between components of interest and generate a score with reference not only to steatosis but also to the inflammation and fibrosis of a hepatic tissue based on digitization of a histological section, without however disclosing a precise method for quantification of quantities of interest with reference to these parameters. The documents US 2017/0215814 A1 and US 2018/0075600 A1 disclose teachings with reference to an automatic analysis of a digitized histological section of a hepatic tissue. Here again, the concept of an accurate quantification of quantities of interest with reference to NASH is missing, rather than the generation of images or scores. Moreover, these two teachings have the deficiency of an absence of precise determination of the portal and central zones, to the detriment of characterization in particular of the fibrosis of such a hepatic tissue.

The invention makes it possible to overcome all or part of the drawbacks previously raised by the conventional histological methods made available to specialized health care personnel or of the earlier techniques, still under development, for automatic processing of histological images. Thus, the invention makes it possible to provide invaluable and reliable aid to any investigator wishing to estimate quantities of interest with a view to generating an indicator facilitating the establishment of an accurate, reliable, and reproducible diagnosis with reference to a human or animal pathology affecting the hepatic tissue, or of the relevance of a treatment with respect to said pathology.

As already mentioned, certain pathologies affecting the hepatic tissue are characterized by a structural remodelling of all or part of the hepatic tissue generally associated with a chronic inflammation of the liver, or even of other organs. The invention allows a very accurate concurrent quantitative morphological analysis of a certain number of tissue components of interest of an organ, and more particularly of the liver, based on a digital representation of histological sections of said organ. The invention thus makes it possible to deliver a multiparametric indicator with reference to the morphology of the components of interest. The invention makes use of a digital representation of a histological section of said organ, describing a plurality of elements each describing a void space resulting from the sectioning or cutting of components such as lipid vacuoles, vessels, or other tears in the tissues, etc., when the histological section is generated. Said components are manifested by surface areas on a two-dimensional representation, when a histological section has been completed.

Among the numerous advantages achieved by the invention, there may be mentioned more particularly those making it possible to:
- considerably reduce the analysis time necessary for establishing a diagnosis of a pathology by an investigator, i.e., to less than one minute depending on the processing power of the device or of the medical imaging system implementing a method according to the invention;
- increase the accuracy and reliability of the measurements of an analyzed sample;
- overcome the variability of results between different investigators, since objective and reproducible measurements are delivered;
- automatically quantify, on the basis of continuous measurements, the four key indicators of NAFLD and NASH namely: steatosis, ballooned hepatic cells, inflammation and fibrosis.

To this end, the invention provides for a method for generating a quantity of interest relating to a human or animal hepatic tissue, based on a digital representation, in the form of a pixel array, of a histological section of a liver. Such a method is implemented by a processing unit of a medical imaging system, said system also including an output human-machine interface. In order to be able to utilize automatically and reproducibly the entirety of the items of information contained in said digital representation, and deliver an objective and accurate aid to health care personnel, the histological section is subjected to a staining step, prior to its digitization, in order to generate said digital representation, said staining causing distinctive stainings of the hepatic tissue, the collagen, the void and the cells forming bile ducts. Such a method includes:
- a step for distinguishing the pixels of said digital representation describing collagen;
- a step for distinguishing the pixels of said digital representation describing the cells of bile ducts;
- a step for identifying the contours of the lumina of the hepatic vessels present in said digital representation and classifying said contours as contours of portal veins or contours of centrilobular veins according to a proximity criterion with pixels of the digital representation distinguished as describing cells of bile ducts;
- a step for determining in the digital representation, portal, central and perisinusoidal zones based on said thus-classified contours;
- a step for quantifying the area of the pixels of the digital representation describing collagen in at least one of said portal, central and perisinusoidal zones;
- a step for generating a quantity of interest describing a degree of fibrosis of the hepatic tissue based on said area of the pixels describing collagen;
- a step for causing an output, via the output human-machine interface of the system, of said quantity of interest.

During the production of the histological section, numerous erythrocytes may be present within lumina of hepatic vessels, compromising the accuracy of the results arising from implementation of such a method. In order to limit the impact of such a phenomenon, the invention provides that the step of staining the histological section prior to its digitization in order to generate said digital representation, can also cause a distinctive staining of the erythrocytes. A method according to the invention thus comprises, prior to the step for identifying the contours of the lumina of the hepatic vessels present in said digital representation, a step for distinguishing the pixels of said digital representation describing erythrocytes, and for modifying the respective values of said pixels by a value describing the void.

By way of example of a preferred implementation, the step of staining the histological section causing distinct stainings of the hepatic tissue, the collagen, the void, and the cells forming bile ducts, can consist of generating jointly, staining with picrosirius red and immunolabelling by CK19.

Similarly, said step of staining the histological section causing a distinctive staining of the erythrocytes can consist of staining with light green SF.

Apart from the generation of a quantity of interest with reference to a degree of fibrosis of a hepatic tissue, such a method according to the invention can comprise a step for quantifying a quantity of interest describing a degree of steatosis of said hepatic tissue. Such a step can consist of:
- identifying the contours of the lumina of the lipid macrovacuoles present in the digital representation;
- adding the surface areas of said lipid macrovacuoles delimited by said contours and generating a total surface area of the lipid macrovacuoles identified within the digital representation;
- normalizing said total surface area of lipid macrovacuoles by the surface area delimited by the largest of the determined contours characterizing the surface area of the entire section of the liver and thus generating the quantity of interest describing a degree of steatosis of said hepatic tissue;
- causing an output, via the output human-machine interface, of said quantity of interest.

Apart from the generation of a quantity of interest with reference to a degree of fibrosis and/or steatosis of a hepatic tissue, a method according to the invention can comprise a step for quantifying a quantity of interest describing a degree of inflammation of said hepatic tissue.

According to a first embodiment, the step of staining the histological section, prior to its digitization in order to generate said digital representation, can cause a distinctive staining of the active macrophages. A method according to the invention can then comprise a step for quantifying a quantity of interest describing a degree of inflammation of the hepatic tissue, consisting of:

identifying the contours of the lumina of the lipid macrovacuoles present in the digital representation;

distinguishing the pixels of said digital representation describing active macrophages;

determining a number of crown-like structures constituted by active macrophages assembled around macrovacuoles in the hepatic tissue;

normalizing said number of crown-like structures per unit of surface area of the hepatic tissue of the histological section;

generating a quantity of interest describing a degree of inflammation of the hepatic tissue based on said number of crown-like structures, optionally normalized;

causing an output, via the output human-machine interface of the system, of said quantity of interest.

By way of advantageous example, the step of staining the histological section causing a distinctive staining of the macrophages can consist of carrying out immunolabelling by F4/80, Mac-2 or CD68 glycoprotein.

According to a second embodiment, the step for quantifying a quantity of interest describing a degree of inflammation of said hepatic tissue can necessitate a step of staining the histological section, prior to its digitization for generating said digital representation, in order to cause a distinctive staining of the hepatic cells in the process of degeneration. A method according to the invention can comprise a step for quantifying a quantity of interest describing a degree of inflammation of the hepatic tissue, consisting of:

distinguishing the pixels of said digital representation describing the hepatic cells in the process of degeneration;

quantifying the area of the pixels of the digital representation describing hepatic cells in the process of degeneration;

normalizing said area by the total area of the hepatic tissue and obtaining a normalized area of the pixels of the digital representation describing hepatic cells in the process of degeneration;

generating a quantity of interest describing a degree of inflammation of the hepatic tissue based on said area of the pixels of the digital representation describing hepatic cells in the process of degeneration, optionally normalized;

causing an output, via the output human-machine interface of the system, of said quantity of interest.

By way of advantageous example, the step of staining the histological section causing a distinctive staining of the hepatic cells in the process of degeneration can consist of Sonic hedgehog immunolabelling combined with staining by hematoxylin.

In order to promote adherence and the interpretation of a quantity of interest, with reference to fibrosis, steatosis, inflammation of the hepatic tissue, quantified by implementation of a method according to the invention, such a quantification step can also consist of generating and recording, in the data memory, a score the integer value of which is representative of said quantity of interest.

According to a second subject, the invention also relates to a computer program product including program instructions, which when they are written to a program memory of a medical imaging system also including a processing unit, an output human-machine interface and a data memory, and interpreted or executed by said processing unit of the latter, cause the implementation of a method for generating a quantity of interest relating to a human or animal hepatic tissue according to the invention and as detailed above.

According to a third subject, the invention also relates to a medical imaging system including a processing unit, an output human-machine interface, a data memory, and a program memory, for which said program memory stores instructions of such a computer program product.

Other characteristics and advantages will become more clearly apparent on reading the following description and on examining the figures accompanying it, in which.

Figure 1:
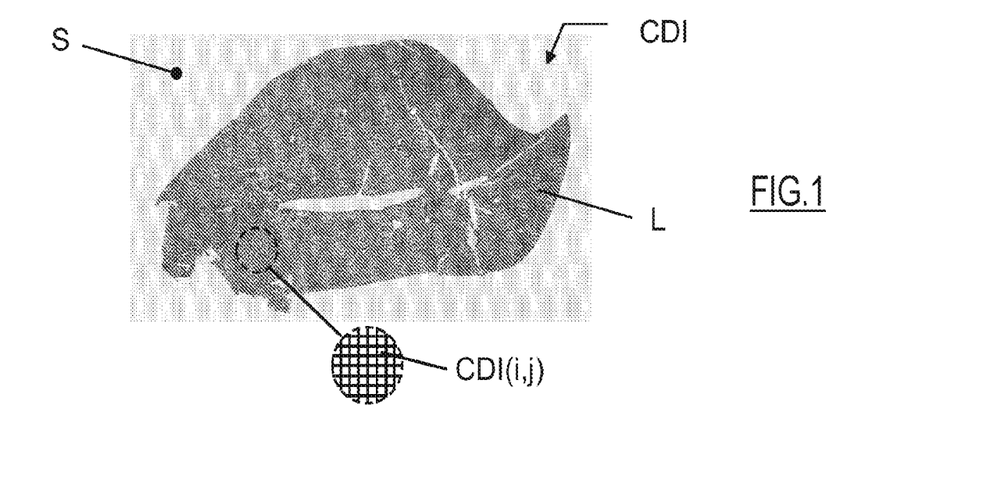
FIG. 1 shows a first digital representation, in the form of an image, of a histological section of a liver affected by NASH, said section being stained beforehand with hematoxylin and eosin.

FIG. 1 shows a first digital representation CDI of a histological section S of a liver L of a patient suffering for example from a remodelling of the hepatic tissue or NASH. Such a first representation CDI generally originates from a process of digitization of a histological section S. A digitized histological section with an enlargement ratio of twenty (×20) delivers said first digital representation CDI in the form of an array with approximately two hundred million pixels CDI(i,j), i and j being indices of integer values for identification of the pixel situated at the $i^{th}$ line and $j^{th}$ column of the CDI array, i.e. according to the example in FIG. 1, a representation in the form of a table or array of fifteen thousand rows to the same number of columns, each element CDI(i,j) of said array encoding a triplet of integer values comprised between zero and two hundred and fifty-five, according to the coding model of RGB (red, green, blue) colours. Such a computerized colour coding is the most compatible with the currently available hardware. In general, computer screens reconstitute a colour by additive mixing from three primary colours, a red, a green and a blue, forming on the screen a mosaic that is generally too small to be distinguished by a human eye. The RGB coding gives a value for each of these primary colours. Such a value is generally encoded on one byte and thus belongs to an integer value interval comprised between zero and two hundred and fifty-five.

Figure 2:
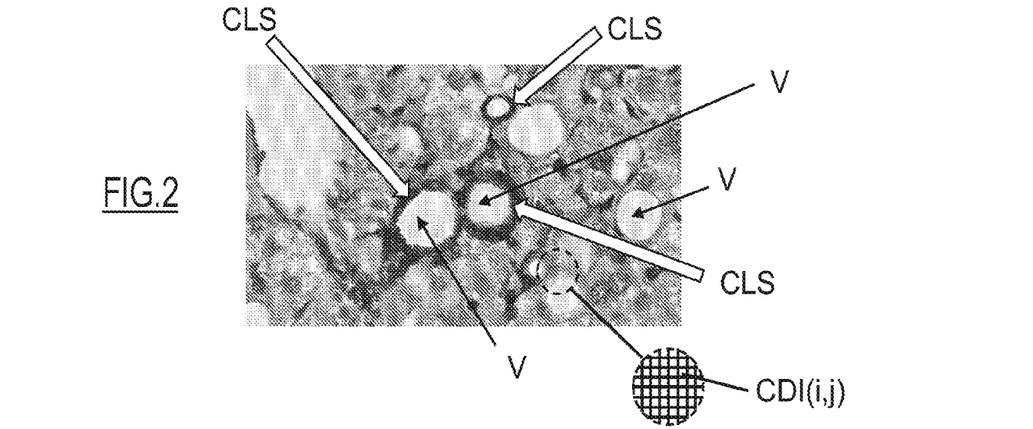
FIG. 2 shows a partial view of a digital representation of a histological section of a liver affected by NASH, illustrating the formation of cells in the form of crown-like structure (active macrophages) around vacuoles, a phenomenon synonymous with an inflammation of the hepatic tissue; said section being stained beforehand by immunohistochemistry with F4/80.
Figure 3:
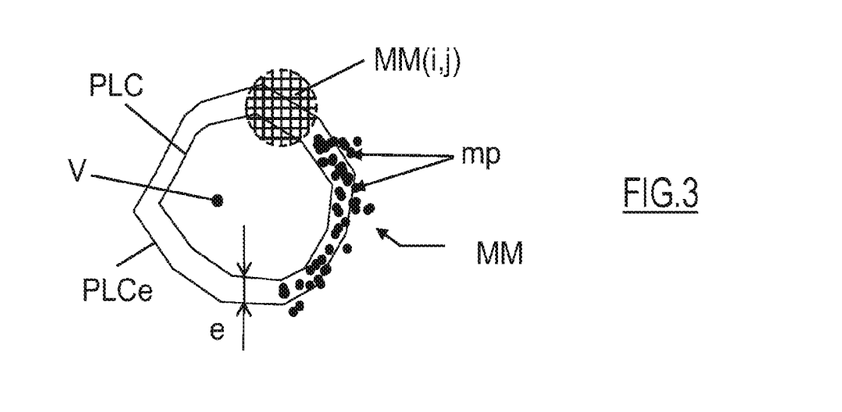
FIG. 3 shows a partial diagrammatic view of a digital representation of a histological section of a liver affected by NASH, illustrating a method for estimating a formation of cells in the form of a crown-like structure around vacuoles.

The representation CDI shows at its centre the parenchyma or hepatic tissue of a liver L. Such a pathological organ includes numerous components in the form of substantially spherical lipid vacuoles V. Following the sectioning performed at the level of the liver, sections of said components V are visible in two dimensions, as components the surface areas of which are similar to discs. Said surface areas of vacuoles V appear as lumina or even spaces describing a void within the hepatic tissue. Such lipid vacuoles V, in this case macrovacuoles, are more clearly visible in FIGS. 2 and 3 illustrating magnifications of digital representations.

The first digital representation CDI of the histological section S of a liver L illustrated in FIG. 1 is representative of a histological section S stained beforehand, in this case for FIG. 1, by hematoxylin and eosin, also known by the abbreviation HE. Such an agent stains the nuclei of hepatic cells blue and the rest of the tissue pink.

Other types of stainings can however equally well be envisaged within the framework of the invention. There may be mentioned in particular staining by picrosirius red, also known by the abbreviation PSR, particularly suitable for showing the presence of collagen, the latter appearing mainly in red while the rest of the hepatic tissue appears predominantly in yellow. In a variant, a Masson's trichrome stain, also known by the abbreviation MTC, can be used, the collagen then appearing in blue. According to another embodiment, performing immunohistochemistry may also be mentioned, consisting of staining a protein with a staining agent. Such staining is particularly advantageous to evidence the presence of macrophage structures in the form of crown-like structures around steatosis vacuoles during their elimination. In the latter case, such a staining prior to the digitization of the histological section S of the liver L can consist of staining the F4/80 protein by a staining agent called "diaminobenzidine", also known by the abbreviation DAB, coupled with the use of hematoxylin as counterstain of the hepatic tissue. However, the invention is not to be considered limited by the use of any particular technique of staining a histological section S, subsequently digitized to create a first digital representation CDI, such as that illustrated by way of non-limitative example in FIG. 1. Said histological section S can thus be the subject of any suitable staining in order to facilitate the determination of components of interest.

When a patient is suffering for example from NASH, the lesion of the liver is revealed by changes in the morphology of certain hepatic tissues. The disease manifests in particular by the formation of lipid vacuoles consisting of an accumulation of lipid material within the cytoplasm of the hepatic cells. Such lesions are revealed, on a first digital representation CDI of a histological section S of a liver L, by void spaces, having relatively circular perimeters, describing transverse sections of lipid vacuoles, as shown in the partial enlargement of the first digital representation CDI shown in FIG. 2. Lumina referenced V are the reflection of this.

The invention consists of offering a particularly valuable aid to health care personnel responsible for estimating a degree of pathology of a patient's liver. Unlike the current techniques according to which certain zones of the section are examined manually by an analyst, the invention provides for the implementation of a method, such as the method 100 described by way of preferred but non-limitative example, in FIG. 4, suitable for automatically analyzing the entirety of the information contained in said histological section S. Such a method 100 is revealed in the form of a computer program product the program instructions of which are intended to be stored in the program memory of a medical imaging system, for example a computer or a computer server, or more generally, any electronic object having a sufficient computation power and/or capable of analysis of digital representations or images of appropriate sizes, taking account of the precision necessary for analysis of a histological section.

Such an electronic object includes, as well as a program memory, a processing unit in the form of one or more microcontrollers or microprocessors. These latter cooperate in particular with a data memory storing digital representations of a histological section S generated by the implementation of a computer program according to the invention, or even by other third party techniques, as well as operating parameters and any other data generated, whether they consist of intermediate data or results, such as a multiparametric indicator I relating to a remodelling of the hepatic tissues, of which a simple consultation informs health care personnel in reaching a diagnosis. Such an electronic object includes, or cooperates with, an output human-machine interface, such that said processing unit can cause the output of graphic results, when said output human-machine interface consists, according to non-limitative examples, of one or more computer screens or any printing peripheral. In a variant or in addition, such an output human-machine interface can include a loudspeaker to deliver a result that can be perceived audibly by a human being.

Such an electronic object can also include an input human-machine interface making it possible for a user to transmit input data, orally, by touch, even gesturally, to parameterize the operation of said electronic object. To this end, such an input human-machine interface can include a keyboard, a touch screen, a camera or even a microphone.

With reference to FIGS. 1 to 4, a method 100 according to the invention is intended to quantify one or more quantities of interest revealing the manifestation and/or the extent of symptomatic phenomena of a pathology. When a plurality of quantities of interest are quantified, the invention provides for these to be revealed in the form of a multiparametric indicator I including different components, communicated to a user in different forms of representation, in particular graphical.

In order to allow the identification of components of interest within a digital representation CDI, as shown in FIG. 2, regardless of the prior staining step of the histological section, a method 100 advantageously includes a prior step (not shown in FIG. 4 for the sake of simplicity) consisting of a processing to "binarize" said first digital representation CDI and to generate a new digital representation, with the same dimensions as those of the first digital representation CDI, but for which each pixel of said new digital representation, referenced by integer indices i and j, comprises a first predetermined value, for example one, when the pixel, having the same indices i and j within the digital representation CDI, consists of a pixel of interest, and a second predetermined value, for example zero, otherwise. Such a new digital representation, which can be referred to as a "hepatic tissue mask" can be generated by any known type of digital processing intended to binarize a digital representation in colour(s), such as the digital representation CDI. Such a digital representation or image is revealed in the form of an array including one and the same number of elements or pixels as the first digital representation CDI of a histological section from which it originates. Said hepatic tissue mask is called "binary" because each of its elements, denoted by two indices or indicators i and j, respectively determining the row and the column of said element or pixel in said mask, includes an integer value chosen from two predetermined values respectively signifying that the pixel CDI(i,j), i.e. of one and the same column j and one and the same row i in the first digital representation CDI, denotes a portion of interest of the organ or not. Such a generation of a hepatic tissue mask can be carried out, according to a preferred but non-limitative embodiment, by finding the greatest contour by implementing, for example, an algorithm such as a "flood-fill" algorithm. By using, preferably but non-limitatively, first and second Boolean values "1" and "0", it is then possible to carry out a simple Euclidean or logical multiplication, by said mask value, in order to take into account, or not, a pixel within a digital representation, having the same dimensions, originating from the first digital representation CDI. Thus, any pixel representing the exterior of the hepatic tissue present in the histological section, or any other pixel captured by the perimeter of said hepatic tissue but describing the lumen of a vein or an artery for example, will not be considered pixels of interest, as will be described hereinafter. The invention is not to be considered limited to the use of said values zero and one. In a variant, other predetermined values could have been chosen to characterize the absence of interest or the interest of such a pixel. Moreover, reliance on the generation and utilization of such a hepatic tissue mask does not constitute an obligation and consequently a limitation for implementing the invention.

Among the particularly significant phenomena, steatosis or formation of lipid vacuoles is particularly symptomatic. A method 100 according to the invention can thus include a first step 110 for estimating or quantifying, based on said first digital representation CDI of the histological section S of the liver L, a non-limitative example of which is described in particular with reference to FIGS. 1 and 2, said representation CDI being written beforehand to the data memory of an electronic object such as a medical imaging system, a first quantity of interest IQ1 describing a degree of steatosis of the hepatic tissue L.

On a digital representation of a histological section of a liver, such a disorder is characterized by the emergence of lipid vacuoles respectively consisting of surface areas having substantially circular perimeters describing lumina within the hepatic tissue. FIG. 1 thus shows a first digital representation CDI of a liver of a patient suffering from NASH. It is noted that to perceive and to count such lipid vacuoles, the respective dimensions of which are of the order of one micron, is an almost impossible task for a human being. The latter generally works using sampling, and their estimate of steatosis is thus partial and not very reproducible. On the other hand, step 110 consists of making use of all the information contained in the digitized histological section S.

One of the subjects of such a step 110 consists of identifying within the digital representation CDI, components of interest V in the form of lipid vacuoles within the hepatic tissue. The step 110 thus comprises a first processing 111 in order to determine, within said first digital representation of the histological section S of the liver L, the pixels CDI(i,j) of the first digital representation CDI describing the surface areas of the respective lumina of said vacuoles V as well as contour polylines PLC delimiting said surface areas. Such a polyline PLC describes, in the form for example of digital vectors, adjacent segments delimiting the perimeter of a surface area captured by said polyline. The processing 111 can thus consist of generating a structure, in the data memory of the electronic object implementing the method 100, in the form of a table of sets of vectors where each entry of said table describes a component of interest within a digital representation having dimensions identical to those of the first digital representation CDI. Such a table can also include a field including a value, in number of pixels, describing the area or the surface captured by the polyline PLC and/or other attributes the respective values of which can enrich the description of the associated components, such as for example, non-exhaustively or non-limitatively, a type of component.

Advantageously but non-limitatively, so as to facilitate the identification of lipid vacuoles in a digital representation of a histological section of a human or animal liver, the processing 111 can also generate another digital representation, which can be referred to as "mask of vacuoles" having the same dimensions as the first digital representation CDI, i.e. including one and the same number of elements or pixels, by row and by column, as said first digital representation CDI. On the other hand, each pixel of said mask of vacuoles describes an integer value, for example comprised between 0 and two hundred and fifty-five, converting the triplet values representing the primary colour scales of the pixels of the first digital representation CDI into integer luminance values. Such a generation can also be accompanied by the implementation of a median or bilateral filter to delete certain aberrations. A thresholding application also makes it possible to thus distinguish the zones describing a void from those describing the hepatic tissue. It then becomes possible to generate via a void area or via a lumen (area), a contour line or polyline delimiting such a lumen. Such an iterative treatment makes it possible to constitute the entirety of the aforementioned contour polylines PLC and to store them in a table in the data memory of the electronic object implementing the method 100. Any other alternative technique for generating such contour polylines PLC could be implemented without departing from the scope of the present invention.

Finally, the step 111 can also consist of testing the morphology of the lumina the contour polylines PLC of which have been generated. In fact, lumina with areas that are too small, i.e., less than, for example, approximately a dozen square micrometres, which could be the manifestation of noise in the first digital representation CDI, or of microvesicles, should not be taken into account. Thus, any area delimited by a polyline PLC below a minimum threshold may result in the deletion of said polyline from the data structure. Similarly, a lumen area above a second threshold, i.e., for example above four thousand square micrometres, then considered to be too large, may be the sign of a lumen of a vessel or a tear in the hepatic tissue. The polyline capturing such a too large surface area may also be deleted from the set of polylines of interest stored in the data memory.

In order to characterize a degree of steatosis, a step 110 of a method 100 according to the invention can include a sub-step 112 for analyzing said contour polylines generated and stored in the data memory, according to at least one predetermined morphological criterion in order to identify, among the surface areas delimited respectively by the latter, the surface areas associated with lipid macrovacuoles.

Such an analysis 112 of a contour polyline PLC can advantageously, but non-limitatively, consist of comparing an eccentricity value of said contour polyline PLC to a predetermined eccentricity threshold, said eccentricity value consisting, for example, of the quotient of a Euclidean division of the Feret mesodiameter by the Feret exodiameter of the contour polyline PLC, said Feret diameters being estimated beforehand. Throughout this document and within the meaning of the invention, by "Feret diameter" is meant an area captured by a contour polyline, the length expressed in number of pixels and optionally normalized, of a straight line passing through said area captured along a given axis. Also, throughout the document and within the meaning of the invention, "Feret mesodiameter" is generally defined as said Feret diameter with the smallest diameter, as opposed to the "exodiameter" which is the maximum Feret diameter. A lumen delimited by a contour polyline PLC may be considered (situation illustrated with reference to 112a in FIG. 4) as being that of a lipid macrovacuole if said eccentricity value is greater than said predetermined eccentricity threshold, for example by a non-limitative value equal to six tenths. Otherwise, the polyline PLC will not be taken into account or used to generate a quantity of interest describing a degree of steatosis.

The analysis 112 of a contour polyline PLC can be complemented or, in a variant, be based on, a test of convexity of the area captured by said contour polyline PLC. Such a test can consist of comparing a convexity value of said contour polyline PLC to a predetermined convexity threshold, said convexity value consisting of the quotient of the division of the surface area of the convex envelope of said contour polyline PLC by the surface area delimited by said contour polyline. Similarly, the surface area delimited by said contour polyline PLC may be considered (situation illustrated with reference to 112a in FIG. 4) as a surface area of macrovacuoles if said convexity value is greater than or equal to said predetermined convexity value, for example, non-limitatively, by a value equal to sixty-five hundredths.

A step 110 of a method 100 according to the invention then includes a sub-step 113a for adding said surface areas of lipid macrovacuoles delimited by the relevant contour polylines and thus generating a total surface area AM covered by lipid macrovacuoles identified within the first digital representation CDI of the histological section S. Such a step 110 can also consist of the normalization 114 of said total surface area of lipid macrovacuoles AM by the surface area delimited by the largest of the determined contours characterizing the surface area of the hepatic tissue. Such a normalized value AM' can thus contribute to the generation of a first quantity of interest IQ1 describing a degree of steatosis of the histological section S of said liver.

In a variant or in addition, such a first quantity of interest IQ1 describing a degree of steatosis of the hepatic tissue of the histological section S can also rely on a quantification of the average value of the size of the macrovacuoles of said liver. The step 110 of a method 100 according to the invention then includes a step, not shown in FIG. 4, for quantifying such an average value on the basis of the surface areas delimited by the contour polylines PLC associated with said macrovacuoles.

In a variant or in addition, such a first quantity of interest describing a degree of steatosis of said hepatic tissue of the histological section S can also rely on an estimation of the microsteatosis value of said hepatic tissue, i.e., a level of microvacuoles present in said liver.

To this end, the step 110 of a method 100 according to the invention can include a sub-step 113b1 for generating and recording, in the data memory of the electronic object implementing said method 100, if said mask has not already been generated in the step 111 at the same time as generating the contour polylines PLC, a digital representation of the histological section S of the liver that will be referred to for simplicity as "mask of the void spaces of interest" MV. Such a digital representation also has the same dimensions as the first digital representation CDI, i.e., it includes as many elements or pixels as the latter. Thus, the pixel MV(i,j), i.e., from row i and column j, corresponds to the pixel CDI(i,j), of the same line i and the same column j, of the first digital representation CDI.

Such a mask of the void spaces of interest MV is however developed based on the first digital representation CDI and the contour polylines PLC determined beforehand in sub-steps 111 and 112. Each pixel MV(i,j) of said mask of the void spaces of interest encodes a first predetermined value, for example equal to one, when said pixel is captured by a contour polyline PLC delimiting a surface area comprised between the predetermined minimum and maximum thresholds, such as, advantageously but non-limitatively, respectively equal to twelve and four thousand square micrometres, or a second predetermined value, for example equal to zero, otherwise. Thus, this is a mask making it possible to generate a binary digital representation, like those mentioned above.

Such a step 110 can then include a sub-step 113b2 consisting of applying an averaging filter to the pixels MV(i,j) of said mask of the void spaces of interest MV in order to generate, and store in the data memory, a new digital representation MVD, having dimensions identical to those of said mask of the void spaces of interest MV, the pixels MVD(i,j) of which encode integer values revealing a density. Such a sub-step 113b2 can then consist of applying a thresholding function of the respective values of said pixels MVD(i,j) in order to take into account only said pixels of interest that encode or describe a density of hepatic tissue below a predetermined threshold, for example having a preferred but non-limitative value of ninety-five percent, and generating a total surface area Am of said pixels of interest describing lipid microvacuoles present on the histological section S of said liver.

The step 110 can consist of normalizing said total surface area Am of lipid microvacuoles by the surface area of the tissue of the histological section S of the liver and generating, in a sub-step 116, a first quantity of interest IQ1 describing a degree of steatosis of the histological section S of said liver L, in the form of a normalized total area of lipid microvacuoles Am'.

Through the implementation of the step 110, a method 100 according to the invention is thus capable of analyzing the entirety of the first digital representation CDI and generating, automatically, accurately, and reproducibly, a first component of an indicator I, in the form of a first quantity of interest describing a degree of steatosis.

In order to promote adherence and facilitate the interpretation of results delivered by such a method according to the invention, the invention provides for such a first quantity of interest IQ1 to be revealed in the form of a score, as is usual practice in this field. To this end, the step 110 can also include an optional sub-step 115 for estimating a first quantity of interest IQ1 describing a degree of steatosis in the form of a steatosis score Sc1 the integer value of which is representative of said degree of steatosis.

To this end, the integer value of said score Sc1 can adopt an integer value comprised between one and three, like the current techniques already described above. This score is directly associated with the number of lipid vacuoles, no longer counted manually in several fields of observation, but by virtue of the invention, based on full analysis of the information contained in the histological section S. By way of example, a score equal to "1" may indicate a normalized area of lipid macrovacuoles and/or microvacuoles present in said histological section S comprised between two and less than thirty-three percent. A score equal to "2" may indicate that such a normalized area of lipid macrovacuoles and/or microvacuoles is comprised between thirty-three and sixty-six percent. Finally, a score equal to "3" may indicate that such a normalized area of lipid macrovacuoles and/or microvacuoles is greater than sixty-six percent. In addition or in a variant, any other mode of conversion of the normalized areas AM' and/or Am', or even any area resulting from a combination of these latter, could be implemented in order to generate the value of such a steatosis score Sc1, without departing from the scope of the present invention.

Still with reference to FIGS. 1 to 4, a method 100 according to the invention is intended to quantify, in a variant or in addition, a second quantity of interest revealing the manifestation and/or the extent of a second symptomatic phenomenon of a pathology. Thus, among the particularly significant phenomena, it is particularly beneficial to estimate fibrosis or the replacement of hepatic cells by scar tissue, to be interpreted jointly with the degree of steatosis, mentioned above with reference to the example of step 110 of a method 100 according to the invention.

Such a method 100 thus advantageously includes a second step 120 for quantifying and recording in a data memory of an electronic object implementing said method 100, a second quantity of interest IQ2, based on said first digital representation CDI of the histological section S of a liver L, describing a degree of fibrosis of said liver.

Such a second step 120 consists of distinguishing, among the pixels describing the liver, those describing collagen. Such a step 120 thus comprises a first sub-step 121 for determining the total surface area AC of the pixels of the first digital representation CDI characterizing the presence of collagen in the hepatic tissue, then, a second sub-step 122 for normalizing said total surface area AC of the pixels of the first digital representation CDI characterizing the presence of collagen by the surface area of the histological section S. Based on such a normalized surface area AC', a sub-step 124 generates a second quantity of interest IQ2 describing a degree of fibrosis of said liver.

In order to be able to implement such a sub-step 121, the histological section S of the liver L was the subject of staining, prior to generating said first digital representation CDI, determined such that the pixels CDI(i,j) of said first digital representation CDI encode a colour palette a first predetermined colour of which reveals a void space, a second predetermined colour reveals the presence of collagen and a third predetermined colour reveals hepatic tissue. As mentioned above, such a staining can advantageously, but non-limitatively, be carried out by using the picrosirius red stain, also known by the abbreviation PSR, or in a variant, Masson's trichrome, also known by the abbreviation MTC. For PSR, the second predetermined stain displaying collagen consists of red, while the third predetermined colour consists of yellow, displaying the hepatic tissue. The first colour, associated with the void, consists of white. For staining with Masson's trichrome, said second predetermined colour would consist of blue and the third would consist of pink. The invention is not to be considered limited by the use of a particular staining method. Any other staining method making it possible to distinguish collagen from the hepatic tissue and from the void space could be used instead.

The distinction between the pixels CDI(i,j) describing collagen or tissue is generally non-trivial. It is sometimes necessary, by way of non-limitative example, to implement a deconvolution operation, referenced 121a in FIG. 4, of the values of said pixels in order to optimize said distinguishing of the pixels describing collagen from those describing the hepatic tissue.

Such a segmentation by deconvolution 121a makes it possible to extract the main components of the first digital representation CDI, so as to maximize the differences of signal between the parts of the image showing different colours. Such a segmentation 121a can make use, for example, of the singular value decomposition technique, also known by the abbreviation SVD. Such a technique relies on the fact that any array A, with coefficients originating from a field K, having real or complex numbers, of dimensions m by n, m and n being two non-zero integers, allows a decomposition such that $A=U\Sigma V^*$ where V is a set of vectors of orthonormal basis Kn, called input vectors, U is a set of vectors of orthonormal basis Km, and $\Sigma$ is the diagonal array, of dimensions m by n, the diagonal coefficients of which are the singular values of the array A, i.e. the eigenvalues of the array $A^*A$. The objective of this decomposition is the calculation of the projection of the array A on one of the singular vectors, one of these directions making it possible to better separate the signal of the collagen (in this case, for staining by PSR, red) from the rest of the tissue (in this case, for staining by PSR, yellow).

The first digital representation CDI can be converted into a colorimetric space such as the space CMY (abbreviation for cyan, magenta, yellow) when said first digital representation CDI reflects a histological section stained by PSR. The values of said first digital representation CDI, the latter being an array of pixels, can be revealed in optical densities, hereinafter expressed by the abbreviation OD (for optical density) such as for three channels C (cyan), M (magenta) and Y (yellow):

$$OD_C = -\log(C/255)$$

$$OD_M = -\log(M/255)$$

$$OD_Y = -\log(Y/255)$$

each component C, M and Y being encoded on one byte.

As the Y channel of the projection is the most promising for the segmentation of the collagen during staining by PSR, the latter is again expressed by an integer value comprised between 0 and 255 by application of the equation $Y = 255 \times 10^{-OD_Y}$.

The step 121a can thus consist of generating a digital representation, having the same dimensions as the first digital representation CDI, the pixels of which thus encode a luminous intensity, such as an image in greyscale, the value of which is generated as described above.

A step 125 can then consist of applying a thresholding filter, for example by using the threshold value equal to fifty, of the respective values of said pixels to generate a new binary digital representation, that will be called "collagen mask" MC, having the same dimensions as the first digital representation CDI, the elements or pixels of which encode a first predetermined value, for example equal to two hundred and fifty-five, when they describe collagen and a second predetermined value, for example equal to zero, otherwise. The total surface area of collagen AC generated in the sub-step 121 can thus consist of determining said surface area covered by the pixels of the mask of the collagen MC the value of which is equal to said first predetermined value.

The invention provides that the step 120 for generating a second quantity of interest IQ2, expressing a degree of fibrosis of a hepatic tissue, may quantify, apart from the total surface area of the collagen AC, optionally normalized AC' by the surface area of the hepatic tissue, the surface area ACps, also optionally normalized ACps' by said surface area of the hepatic tissue, of the perisinusoidal collagen alone. The latter relates to the collagen that forms, within the context of a pathological liver, around the sinusoids, structural elements of the liver connecting the central veins and the portal veins. Such a perisinusoidal collagen is generally low-density, unlike, for example, the peri-vascular collagen of higher densities.

A method 100 according to the invention proposes a first embodiment for quantifying the surface area of the perisinusoidal collagen alone present in the histological section S from which the first digital representation CDI originated. According to this first embodiment, the step 120 can include a sub-step 126a consisting of the application of an averaging filter, the window of which can be parameterized, by way of non-limitative examples, at four or five microns, to the pixels of said collagen mask MC, generated in the sub-step 125. Said sub-step 126a thus generates and stores, in the data memory of the electronic object implementing the method 100, a new digital representation MCD, having the same dimensions as the representations CDI and MC, the pixels of which encode the integer values revealing a density of the collagen detected in the hepatic tissue. Such a density can consist of an integer-value encoding, encoded on one byte. The high densities are expressed by values above a predetermined threshold, parameterized, by way of non-limitative example, at a value equal to fifty. Conversely, the low densities are those expressed by values below said threshold. The step 120 can then include a sub-step 126b consisting of applying a thresholding of said pixels of the digital representation MCD, to consider only pixels of interest describing a collagen density below said predetermined threshold and generating a total surface area ACps covered by the pixels the value of which is below said threshold. Such a surface area ACps of collagen of low density can be estimated as being the surface area of the perisinusoidal collagen. Such a surface area can optionally be normalized, in the sub-step 122, by the surface area of the hepatic tissue and thus be expressed in the form of a percentage of said surface area of said hepatic tissue as a normalized surface area ACps'.

In a variant, the invention proposes a second embodiment for quantifying the surface area of the perisinusoidal collagen alone present in the histological section S from which the first digital representation CDI originated. According to this variant, the invention provides for said histological section S to be the subject of staining of a type such that the third predetermined colour revealing the hepatic tissue consists of a first tint or predetermined shade, for example brown, when said pixels describe the portal space and a second tint or shade, for example still yellow, otherwise. Such a staining can result from a double immunolabelling. Determining 121 the total surface area ACps of the pixels of the first digital representation CDI characterizing the presence of perisinusoidal collagen concerns only said pixels adjoining those describing the portal space of the liver, appearing in this embodiment, according to said first tint or shade.

The invention also proposes a second embodiment of the step 120 for quantifying the presence of collagen present in the histological section S from which the first digital representation CDI originated. The main objective of this second embodiment is to quantify accurately and automatically such a presence of collagen in three particular zones of interest of the histological section, namely the portal space, the central space and the perisinusoidal space. For Pierre Bedossa, major player in the analysis of NASH (Liver International, 2017), such a quantification of the collagen within these three zones is fundamental for aiding the diagnosis of such a pathology. According to this variant, the invention provides for said histological section S to be the subject of a staining or staining step of such a type that the third predetermined colour revealing the hepatic tissue consists of a predetermined first tint or shade, for example brown, when said pixels describe cells forming bile ducts and a second tint or shade, for example still yellow, otherwise. Such a staining can result from immunolabelling with cytokeratin 19, also known by the abbreviation CK19.

This second embodiment of the step 120 consists mainly of:

a step for distinguishing, within said first digital representation CDI, the pixels describing collagen;

a step for identifying the contours of the lumina of the hepatic vessels present in a digital representation CDI of a histological section of a liver L;

a step for distinguishing, within the first digital representation CDI, the pixels describing cells of bile ducts;

classifying the contours of the lumina of the hepatic vessels identified as contours of lumina of portal veins when said contours are close to pixels characterizing the presence of cells of bile ducts or as contours of lumina of centrilobular veins otherwise;

determining the portal, central and perisinusoidal spaces, within the first digital representation CDI, as respectively the pixels captured by the contours of lumina of portal veins, the pixels captured by the contours of lumina of central veins and the pixels characterizing hepatic tissue, apart from hepatic vessels;

a step for quantifying the respective areas of the pixels characterizing the presence of collagen of the first digital representation CDI in each of the three zones of the hepatic lobule, said areas being able to be normalized with respect to the area of the hepatic lobule and thus to deliver a quantity of interest describing a degree of fibrosis of said hepatic lobule of the histological section.

In order to distinguish, within said first digital representation CDI, the pixels describing collagen, the step 120 of a method 100 according to the invention advantageously includes steps 121a and 125, similar to those described above. Said step 121a consists of generating a digital representation, having the same dimensions as the first digital representation CDI, each pixel of which encodes a luminous intensity generated, for example, by implementing a deconvolution operation. The step 125 consists of generating a collagen mask MC, in the form of a binary representation having the same dimensions as the first digital representation CDI.

In order to identify the contours of the lumina of the hepatic vessels present in the first digital representation CDI, the step 120 can include a step 127a for distinguishing the pixels CDI(i,j) characterizing such lumina. Like the processing 111 described above with reference to the quantification of steatosis, such an operation consists of determining contour polylines PLCV delimiting said lumina. These latter describe, for example in the form of digital vectors, adjacent segments each delimiting the perimeter of a surface area captured by said polyline. The processing 127a can thus consist of generating and storing, in the data memory of the electronic object implementing the method 100, a data structure in the form of a table of sets of vectors where each entry of said table describes a component of interest within a digital representation having dimensions identical to those of the first digital representation CDI. Such a table can also include a field including a value, in number of pixels, describing the area or the surface captured by the polyline and/or other attributes the respective values of which can enrich the description of the associated components, such as for example, non-exhaustively or non-limitatively, a type of hepatic vessel.

Advantageously but non-limitatively, so as to facilitate the identification of hepatic vessels in a digital representation of a histological section of a human or animal liver, the processing 127a can also generate a digital representation MVH, called "mask of the hepatic vessels" having the same dimensions as the first digital representation CDI, i.e., including one and the same number of elements or pixels, by row and by column, as said first digital representation CDI. Each pixel of said mask of the hepatic vessels describes an integer value, for example comprised between zero and two hundred and fifty-five, converting the triplet values representing the primary colour scales of the pixels of the first digital representation CDI into integer luminance values. Such a generation can also be accompanied by the implementation of a median or bilateral filter to suppress certain aberrations. A thresholding application also makes it possible to thus distinguish the zones describing a void from those describing the hepatic tissue. It then becomes possible to generate via a void area or via a lumen (area), a contour line or polyline delimiting such a lumen. Such an iterative processing makes it possible to constitute the entirety of the aforementioned contour polylines PLCV. Any other alternative technique for generating such contour polylines could be implemented without departing from the scope of the present invention.

The step 127a can also consist of testing the morphology of the lumina the contour polylines PLC of which have been generated. In fact, lumina with areas that are too small, i.e., less than, for example, two thousand eight hundred square micrometres, which could be the manifestation of noise or lipid vesicles, should not be taken into account. Thus, any area delimited by a polyline below a minimum threshold may result in the deletion of said contour polyline from the data structure PLCV.

A binary mask of the hepatic vessels MVH is constituted by assigning to each pixel of said mask MVH of the hepatic vessels, for example the value "0" or nil value, signifying the Boolean value "False" when said pixel is captured or encircled by a contour polyline PLCV, or the value "255" signifying the Boolean value "True" when said pixel is not captured or encircled by such a polyline of contour PLCV. The invention provides optionally that the generation of said binary mask MVH, describing the areas of the hepatic vessels, can be the subject of an additional mathematical morphology operation intended to dilate the size of said areas, for example according to a circular deformation with a determined radius, for example a value of one hundred micrometres.

Implementation of the step 127a for generating the contour polylines PLCV of the vessels then optionally the mask of the hepatic vessels MVH, can be changed or falsified by a significant presence of erythrocytes in the lumina of said vessels. With a step of staining with picrosirius red (PSR) of the histological section from which the first digital representation CDI originates, said erythrocytes are coloured yellow, like the hepatic tissue. The prior segmentation described in step 127a for distinguishing the hepatic tissue from the void corresponding to the lumina of the vessels can thus be falsified by the presence of these latter. In order to resolve this technical problem, the invention provides for the preparation of the histological section by adding to the PSR a light green SF stain. Such a preparation, or "staining", makes it possible to avoid affecting the staining of the hepatic tissue by the picrosirius red. Said tissue remains stained yellow, the collagen, red. In contrast, the erythrocytes appear in green under the effect of the light green SF. The step 127a consists of implementing a processing, prior to the generation of the contour polylines PLCV, for segmenting or distinguishing the pixels CDI(i,j) associated with the erythrocytes and replacing the respective values of said pixels so that the latter describe the void. The first digital representation CDI thus "cleaned" can be analyzed to generate the contour polylines PLCV, as described above.

In order to make it possible to identify the portal spaces in the first digital representation CDI, the invention provides for distinguishing, within the first digital representation CDI, the pixels CDI(i,j) describing cells of bile ducts. The step 120, according to this second embodiment, includes a step 127b for constituting a digital representation MCK19, called "bile ducts mask" having the same dimensions as the first digital representation CDI, i.e., including one and the same number of elements or pixels, by row and by column, as said first digital representation CDI. Constituting such a binary mask is made possible by immunolabelling by CK19, or by any other marker capable of distinctively staining the cells of the bile ducts, of the histological section. As with the pixels describing the collagen, such distinguishing is carried out by deconvolution, according to a technique similar to that described above, with reference to the generation of the collagen mask MC. Such a segmentation 127b can make use, for example, of the singular value decomposition technique. The objective of this decomposition is to separate the signal of the cells of the bile ducts, appearing in brown, for staining by PSR, or light green SF, and immunolabelling CK19, from the rest of the tissue or from the collagen, appearing respectively in yellow and in red, for staining by PSR of the histological section.

The first digital representation CDI can be converted into a colorimetric space such as the space CMY (abbreviations for cyan, magenta, yellow) when said first digital representation CDI reflects a histological section stained by PSR. The values of said first digital representation CDI, the latter being an array of pixels, can be revealed in optical densities, hereinafter expressed by the abbreviation OD (for optical density) such as for three channels C (cyan), M (magenta) and Y (yellow):

$OD_C = -\log(C/255)$ $OD_M = -\log(M/255)$ $OD_Y = -\log(Y/255)$ each component C, M and Y being encoded on one byte.

As the Y channel of the projection is the most promising for the segmentation of the bile ducts during staining by PSR, the latter is again expressed by an integer value comprised between 0 and 255 by application of the equation $Y = 255 \times 10^{-CD_Y}$.

The step 127b can thus consist of generating a digital representation, having the same dimensions as the first digital representation CDI, the pixels of which thus encode a luminous intensity, such as an image in greyscale, the value of which is generated as described above, then by applying a thresholding filter, for example by using the threshold value equal to fifty, of the respective values of said pixels to generate the binary mask of the bile ducts MCK19, the pixels of which encode a first predetermined value, for example equal to two hundred and fifty-five, when the corresponding pixels CDI(i,j) describe bile ducts and a second predetermined value, for example equal to zero, otherwise. Such a step 127b can also consist of the implementation of a mathematical morphological operation of the closing type on said mask MCK19, such that the latter includes not only distributed pixels or ranges of non-adjacent pixels associated with cells of bile ducts but homogeneous pixel zones, solid and closed with smooth contours. By way of example, such a mathematical morphological operation can consist of the implementation of an image processing algorithm from OpenCV or equivalent, for which a circular kernel of approximately ten microns may be chosen. Certain contours enclosing an area smaller than a predetermined threshold, for example equal to two hundred microns, may be deleted from said mask MCK19; the last pixels thus captured will adopt the predetermined value, meaning that said pixels are no longer associated with cells of bile ducts.

In order to classify the contours of the lumina of the hepatic vessels as contours of lumina of portal or centrilobular veins, the step 120 includes a step 127c consisting of as it were superimposing the contour polylines PLVC, generated in the step 127a, onto said binary mask MCK19 and to assign to said contour polylines PLCV, a determined attribute characterizing a portal vein, if and only if, such a contour polyline PLCV is close, within a determined radius, for example of the order of approximately one hundred microns or micrometres, to an area or a set of pixels of the mask MCK19 associated with cells of bile ducts. Conversely, a second determined attribute, characterizing a centrilobular vein, will be assigned to all contour polylines PLCV distant from an area or a set of pixels of the mask MCK19 associated with cells of bile ducts.

In order to determine the portal, central and perisinusoidal zones of the first digital representation CDI, the step 127c then generates three masks, i.e., three digital representations MZP, MZC, MZPS, having the same dimensions as the first digital representation CDI, i.e., including one and the same number of elements or pixels, by row and by column, as said first digital representation CDI.

Each pixel of a first mask, called "mask of portal zones" MZP, includes an integer value, for example a first value equal to "0" or nil value, signifying the Boolean value "False", when said pixel of the mask MZP is not captured or encircled by a contour polyline PLCV associated with a portal vein, or a second value equal to "255" signifying the Boolean value "True", otherwise.

Each pixel of a second mask, called "mask of central zones" MZC, also includes an integer value, for example a first value equal to "0" or nil value, signifying the Boolean value "False", when said pixel of the mask MZC is not captured or encircled by a contour polyline PLCV associated with a centrilobular vein, or a second value equal to "255" signifying the Boolean value "True", otherwise.

Finally, the step 127c generates a third binary mask, called "perisinusoidal zones mask" MZPS, by implementing a Boolean logic operation such that MZPS=MVH AND (NOT MZP) AND (NOT MZC).

In other words, the mask MZPS, describing the perisinusoidal zones of the hepatic tissue, includes pixels with the value "True" associated with said hepatic tissue and with the value "False" associated with the portal or central zones.

Each pixel CDI(i,j) of the first digital representation CDI corresponding to a pixel of the binary masks MZC, MZP and MZPS, the value of which is equal to the value "True" belongs to one of the three zones of interest, namely a portal, central or perisinusoidal zone.

Having available the three masks MZP, MZC and MZPS respectively describing the three zones of interest described above, as well as the collagen mask MC generated in step 125, the step 120 according to this second particularly advantageous embodiment includes a step 128 for quantifying the collagen present in each of said three zones of interest. Such a quantification consists of calculating the area of the collagen for all the pixels of the collagen mask MC and if, and only if, said corresponding pixels in one of the masks MVH, MZP, MZC and MZPS describe the value "True". The step 128 thus consists of calculating an area AC of collagen with respect to the hepatic tissue, apart from hepatic vessels, an area of collagen ACp in the portal zones, an area of collagen ACc in the central zones and an area of collagen ACps in the perisinusoidal zones. Such areas can be normalized in a step 124 such as described above, to generate a second quantity of interest IQ2 describing a degree of fibrosis of said liver. This optional normalization of the areas of collagen can be carried out with respect to the total area of the section of the liver or the area of each zone concerned based on the appropriate mask MZP, MZC, MZPS, MVH. The step 124 can thus generate normalized areas AC', ACp', ACc' and/or ACps' associated respectively with the hepatic tissue, apart from hepatic vessels, with the portal zones, with the central zones and with the perisinusoidal zones.

Through the implementation of the step 120, a method 100 according to the invention is thus capable of analyzing the entirety of the first digital representation CDI and generating, automatically, accurately, and reproducibly, a second component of an indicator I, in the form of a second quantity of interest IQ2 describing a degree of fibrosis.

In order to facilitate adherence and the interpretation of results delivered by such a method according to the invention, the invention provides for such a quantity of interest IQ2 to be revealed in the form of a score, as is usual practice in this field. To this end, the step 120 includes an optional sub-step 123 for estimating a second quantity of interest IQ2 describing a degree of fibrosis of the hepatic tissue of the histological section S in the form of a fibrosis score Sc2 the integer value of which is representative of the degree of fibrosis of the liver L.

The integer value of said score Sc2 can adopt an integer value comprised between zero and four, like the current techniques described above. This score is directly associated with the presence of collagen, no longer counted manually in several fields of observation, but by virtue of the invention, based on full analysis of the information contained in the histological section S, more particularly the areas AC, ACps, ACp, ACc optionally normalized, as described above. By way of example, a score equal to "0" may reveal an absence of collagen in the whole of the histological section S of a liver, i.e., a normalized surface AC' less than a few percent. A score equal to "1" or "2" may depend on thresholds applied to the normalized surface ACps' of the perisinusoidal collagen. A score equal to "3" or "4" may depend on thresholds applied to the normalized surface AC' of the collagen in the hepatic tissue, a score equal to "4" can illustrate a very advanced fibrotic state of the liver. In addition or in a variant, any other mode of conversion of the normalized areas AC', ACp', ACc' and/or ACps', or even any area resulting from a combination of these, could be implemented in order to generate the value of such a fibrosis score Sc2, without departing from the scope of the present invention.

Still with reference to FIGS. 1 to 4, a method 100 according to the invention is intended to generate a multiparametric indicator I, revealing the manifestation and/or the extent of another symptomatic phenomenon of a pathology. Thus, among the particularly significant phenomena, it is particularly beneficial to quantify inflammation of the hepatic cells, to be optionally interpreted jointly with the degrees of steatosis and/or of fibrosis, respectively mentioned above with reference to the steps 110 and 120 of a method 100 according to the invention.

Thus, such a method 100 can advantageously include a third step 130 for generating and recording in a data memory of an electronic object implementing said method 100, a third quantity of interest IQ3, based on said first digital representation CDI of the histological section S of a liver L, describing a degree of inflammation of the tissue of said liver.

Inflammation of the hepatic tissue is accompanied by swelling or "ballooning" of a part of the hepatic cells. This swelling is a key structural change in the hepatic cells falling within the characterization of NASH. The current analysis of the hepatic cells exhibiting ballooning or swelling is at present carried out manually on observation fields of a histological section including hepatic tissue. For pathologists, this partial quantification is based on the only morphological criterion enabling them to distinguish a ballooned cell visually, without too much uncertainty. Such an analysis can only be carried out on cells at the end of the cell cycle, i.e., which have lost almost all of their cytoplasm. In order to be able to quantify automatically and over the whole of the hepatic tissue in question, all the hepatic cells in the process of degeneration, a method 100, according to the invention, can include a step 130 for generating a quantity of interest IQ3 describing the inflammation of a hepatic tissue.

In order to identify automatically such swelled or ballooned cells, the histological section of the liver L is treated beforehand with Sonic hedgehog (SHH) immunolabelling, counter-stained with hematoxylin. Such a preparation, or "staining", makes it possible to differentiate the hepatic cells in the process of degeneration from the rest of the hepatic tissue. Any other immunolabelling of the histological section generating the same technical effect could be used.

The step 130 includes a sub-step of segmentation 131e of the pixels of a first digital representation CDI obtained by digitization of said histological section. Such a segmentation can be carried out by deconvolution, according to a technique similar to that described above with reference to CK19 immunolabelling. The step 131e thus consists of automatically distinguishing and quantifying all the pixels CDI(i,j) describing hepatic cells in the process of degeneration, whether they are at the start or in the middle of their degeneration cycle. Like distinguishing the immunocytes by virtue of the CK19 staining, the segmentation 131e of pixels CDI(i,j) describing the hepatic cells in the process of degeneration can also consist of constituting 131f a binary mask MHD called "mask of the hepatic cells in the process of degeneration". The step 130 then includes a step 131g of calculating the area AHD described by the entirety of the pixels of said mask MHD describing the hepatic cells in the process of degeneration. Such an area AHD can be normalized AHD' in a step 132, by the total area of the hepatic tissue and thus constitute the third quantity of interest IQ3 in a step 134.

In a variant or in addition, an inflammation of the hepatic tissue can be quantified, according to the invention, by detecting active macrophages, forming crown-like structures, with a view to eliminating the lipid vacuoles, for example detected by step 110 of the method 100.

The step 130 can consist mainly of determining, in a sub-step 131d, a number NCLS of such structures of active macrophages mp in the form of crown-like structures around macrovacuoles V in the tissue of the liver L, then, advantageously but non-limitatively, normalizing said number NCLS by unit of surface area of the tissue of the histological section S of the liver in a sub-step 132. FIG. 2 shows, by way of non-limitative example, a partial enlargement of a first digital representation CDI, such as that illustrated by FIG. 1, after having been the subject of a specific immunolabelling, known by the abbreviation IHC. Such a technique makes it possible to locate proteins in the cells of a tissue section, via the detection of antigens by means of antibodies, in this case the F4/80 glycoprotein. In a variant, the step of staining the hepatic tissue of the histological section, in order to highlight said active macrophages, can consist of the application of Mac-2, CD68, or any other suitable immunolabelling. Said FIG. 2 clearly shows macrovacuoles V present in the hepatic cells. They appear in the form of discs of light colour, or even white. Some of said macrovacuoles V are encircled by a dark-coloured annular structure. Such crown-like structures CLS are formed by active macrophages mp. FIG. 3 shows in simplified fashion a macrovacuole V, in a partial binary representation MM, the perimeter of which is represented by a polyline PLC. Around said polyline PLC are accumulated macrophages mp symbolized by black dots. Said FIG. 3 will be described in greater detail hereinafter.

The step 130 of a method 100 according to the invention can thus generate, in a sub-step 134, the third quantity of interest IQ3 describing a degree of hepatic inflammation of the tissue of the histological section S of said liver L on the basis of the value of the number NCLS of crown-like structures CLS or of the normalized value NCLS' of said number NCLS, respectively quantified in sub-steps 131d and 132.

As with the estimation of fibrosis described with reference to step 120 of a method according to the invention, the step 130 for quantifying a degree of inflammation of the liver L, can implement, according to a preferred but non-limitative embodiment, a sub-step 131a consisting of carrying out an operation of deconvolution of the values of the pixels of the first digital representation CDI, a partial enlargement of which is shown in FIG. 2, in order to optimize said distinguishing of the pixels describing macrophages from those describing the hepatic tissue. Under the effect of the F4/80 immunolabelling, the pixels CDI(i,j) of the colour image CDI encode a colour palette, expressed as the RGB coding, such that a first predetermined colour, in this case white, reveals any void space or lumen of vacuole V, a second predetermined colour, in this case brown, reveals the presence of macrophages mp, and a third colour, in this case blue, reveals the cells of the hepatic tissue. The invention is not to be considered limited by the use of this particular colour palette.

A segmentation by deconvolution 131a makes it possible to extract the main components of the first digital representation CDI, so as to maximize the differences of signal between the parts of the image showing different colours. Such a segmentation 131a can make use, for example, of the singular value decomposition method, also known by the abbreviation SVD. As detailed above with reference to the example of sub-step 121a for fibrosis, such a technique relies on the fact that any array A, with coefficients originating from a field K having real or complex numbers, of dimensions m by n, these latter being two non-zero integers, allows a decomposition such that A=UΣV* where V is a set of vectors of orthonormal basis Kn, called input vectors, U is a set of vectors of orthonormal basis Km, and Σ is the diagonal array, of dimensions m by n, the diagonal coefficients of which are the singular values of the array A, i.e. the eigenvalues of the array A*A. The objective of this decomposition is the calculation of the projection of the array A on one of the singular vectors, one of these directions making it possible to better separate the signal of the macrophages, in this case, for F4/80 immunolabelling, from the rest of the tissue, in this case, for hematoxylin counter-staining, blue.

The first digital representation CDI can if necessary be converted into a colorimetric space such as the space CMY (abbreviations for cyan, magenta, yellow). The values of said first digital representation CDI, the latter being a mask of pixels, can be revealed in optical densities, hereinafter expressed by the abbreviation OD, such as for three channels C (cyan), M (magenta) and Y (yellow):

$$OD_C=-\log(C/255)$$

$$OD_M=-\log(M/255)$$

$$OD_Y=-\log(Y/255)$$

each component C, M and Y being encoded on one byte.

For staining by DAB/H (abbreviation for diaminobenzidine, counter-stained with hematoxylin) of the histological section S, from which the first digital representation CDI originates, the red, green, blue coding, also known by the abbreviation RGB, each component R, G, B is encoded on one byte. The projection being the most promising for the segmentation of the macrophages is the channel or the component B. The latter is again expressed by an integer value comprised between 0 and 255 by application of the equation: $B=255\times10^{-OD_C}$.

The sub-step 131a makes it possible to generate, and to store, in the data memory of the electronic object implementing the method 100, a digital representation having the same dimensions as the first digital representation CDI, the pixels of which thus encode a luminous intensity, such as an image in greyscale, the value of which is generated as described above.

Figure 4:
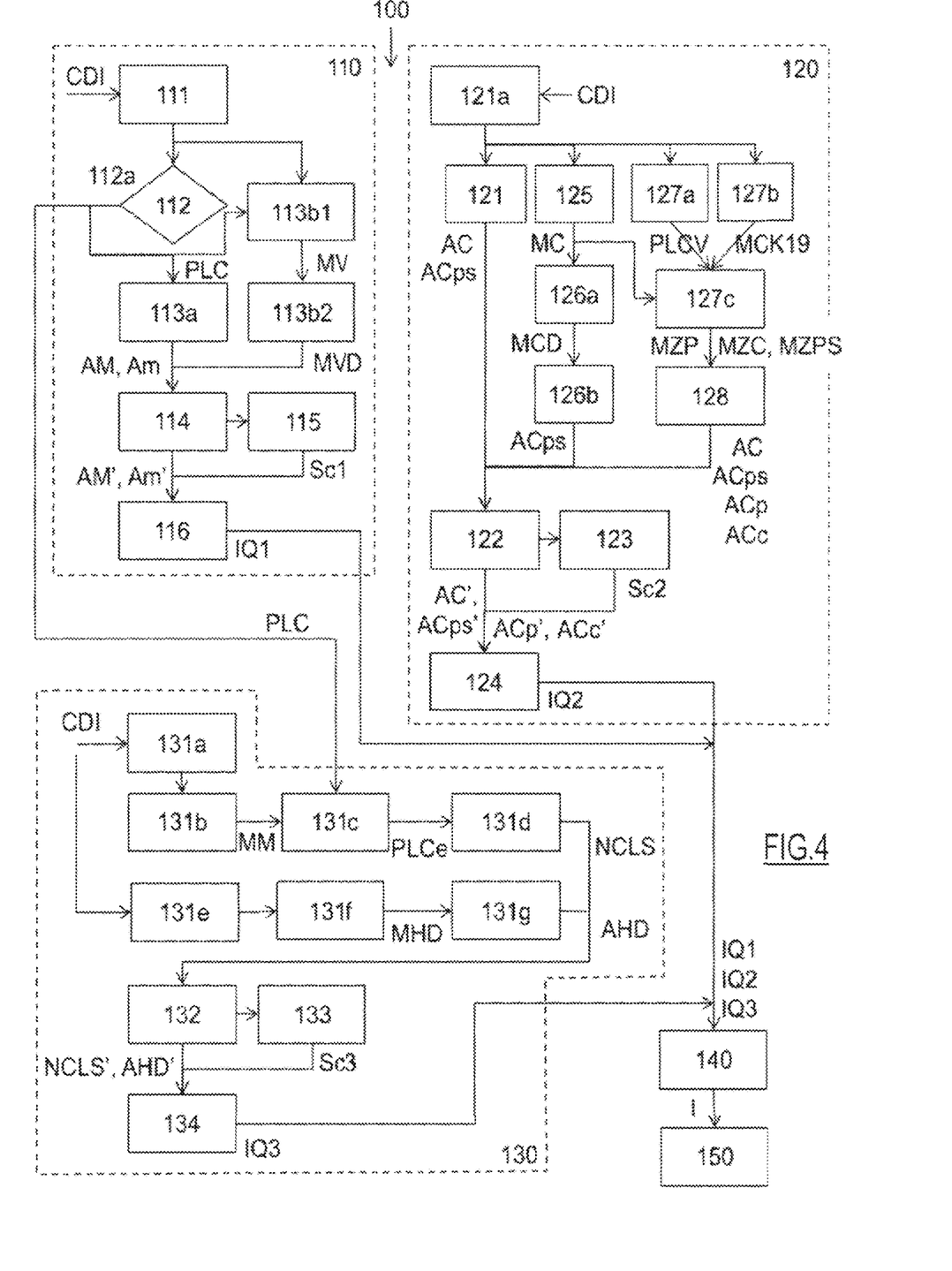
FIG. 4 represents a simplified flow chart of an advantageous but non-limitative embodiment of a method for generating one or more quantities of interest with reference to a hepatic tissue according to the invention.

The step 130 can then include a sub-step 131b for applying a filter by thresholding to the pixels of said digital representation in greyscale, by using, for example, the threshold value equal to sixty-four. A new binary digital representation MM is generated. The latter will be referred to as "mask of the macrophages". Like the other digital representations, optionally binary, generated in steps 110 and 120 of a method 100 according to the invention, the binary digital representation MM has the same dimensions as the first digital representation CDI. Its elements or pixels MM(i,j) thus encode a first predetermined value, for example equal to two hundred and fifty-five, when they describe macrophages, and a second predetermined value, for example equal to zero, otherwise. In order to test if a structure of macrophages in a crown-like structure CLS surrounds a macrovacuole V, as indicated in FIGS. 3 and 4, the step 130 of a method 100 according to the invention can include a sub-step 131c for generating a polyline with a crown-like structure by dilatation PLCe of each contour polyline PLC, determined beforehand during implementation of the step 110 in order to estimate the first quantity of interest IQ1 describing a degree of steatosis of the tissue of the liver L and associated with a macrovacuole V, such that the pairs respectively formed by a contour polyline PLC and a polyline of a crown-like structure obtained by dilatation PLCe respectively describe annular assemblies of a predetermined thickness e, with an equal value, optionally normalized by number of pixels, by way of advantageous but non-limitative example, of the order of thirteen micrometres. Such annular assemblies define the pixels of interest among the pixels MM(I,j) of the mask of the macrophages MM. The sub-step 131c then consists of assessing, in each annular assembly, a proportion of pixels of interest describing the presence of macrophages mp. Such a proportion can be obtained by evaluation of the quotient of the division of the surface area covered by said pixels of interest describing macrophages mp within the annular assembly by the surface area of all the pixels of interest composing said annular assembly.

The sub-step 131d intended to quantify the number NCLS of structures of macrophages in the form of crown-like structures CLS can consist of incrementing a counter, the current value of which is stored in the data memory of the electronic object implementing the method 100, of crown-like structures if, and only if, said proportion of pixels of interest in an annular assembly describing the presence of macrophages is above a predetermined threshold, for example a value equal to forty percent.

The step 130 can thus estimate, in a sub-step 134, a third quantity of interest IQ3, describing a degree of inflammation of the tissue of the liver based on the value NCLS of said counter of crown-like structures CLS, or even its normalized value NCLS' per unit of surface area of the hepatic tissue.

In order to promote adherence and ease of interpretation of results delivered by such a method according to the invention, the invention provides for such a quantity of interest IQ3 to be revealed in the form of a score, as is usual practice in this field. To this end, the step 130 can also include an optional sub-step 133 for estimating a third quantity of interest IQ3 describing a degree of inflammation of the tissue of the histological section S of said liver in the form of an inflammation score Sc3 the integer value of which is representative of the degree of inflammation of the tissue of the histological section S of said liver L.

To this end, the integer value of said score Sc3 can adopt an integer value, like the current techniques described above. Any mode of conversion of an area of hepatic cells in the process of degeneration AHD or of ballooned cells, area optionally normalized AHD', or any conversion of the number NCLS of structures of macrophages in the form of crown-like structures, optionally normalized NCLS', could be implemented in order to generate the value of such an inflammation score Sc3 without departing from the scope of the present invention.

Regardless of the quantities of interest IQ1, IQ2, or even IQ3, optionally associated with scores, describing respectively a degree of steatosis, of "ballooning", of fibrosis and of inflammation of the hepatic tissue in question relating to a histological section S from which the first digital representation CDI originates, a method 100 according to the invention includes a step 140 for generating graphical representations of said first, second, or even third, estimated quantities of interest. Such a graphical representation can consist of a simple string of alphanumeric characters for encoding a numerical value of such a quantity of interest. In a variant or in addition, it can consist of generating a bar of a histogram the length or the height of which reveals such a numerical value, or even an axis of a Kiviat graph, radar chart, star chart, or even spider chart, beneficial for representing in a two-dimensional plane at least three quantities of interest, in the form of multivariate data, each axis, starting from one and the same point, representing one of said quantities of interest. The invention also provides that all or part of the digital representations generated, in addition to the first digital representation CDI of a histological section S, are able to be delivered or displayed, to a user of an electronic object suitable for implementing a method 100 according to the invention, jointly with one or more of said estimated quantities of interest. Thus, a graphical representation generated in step 140 can be simple or complex, according to the substance of the content generated. It can also be individualized, i.e., pertaining to one of the quantities of interest generated, or collective, i.e., jointly relating to several of said quantities of interest IQ1, IQ2, IQ3 estimated by the steps 110, 120, or even 130, of a method 100 according to the invention in order to compose a graph.

Finally, a method 100 according to the invention comprises a step 150 for causing a display of one or more of said graphical representations by the output human-machine interface of an electronic object implementing said method 100, such as a medical imaging system mentioned above.

The invention claimed is:

1. Method for generating a quantity of interest relative to a human or animal hepatic tissue, based on a digital representation in the form of a pixel array, of a histological section of a liver, said method being implemented by a processor of a medical imaging system, said system also including an output human-machine interface, wherein:
the histological section is the subject of a staining step, prior to its digitization, in order to generate said digital representation, said staining causing distinctive stainings of the hepatic tissue, the collagen, the void and the cells forming bile ducts;
said method includes:
a step for distinguishing the pixels of said digital representation describing collagen;
a step for distinguishing the pixels of said digital representation describing the cells of bile ducts;
a step for identifying the contours of the lumina of the hepatic vessels present in said digital representation and classifying said contours as contours of portal veins or contours of centrilobular veins according to a proximity criterion with pixels of the digital representation distinguished as describing cells of bile ducts;
a step for determining in the digital representation, portal, central and perisinusoidal zones based on said thus-classified contours;
a step for quantifying the area of the pixels of the digital representation describing collagen in at least one of said portal, central and perisinusoidal zones;
a step for generating a quantity of interest describing a degree of fibrosis of the hepatic tissue based on said area of the pixels describing collagen;
a step for causing an output, via the output human-machine interface of the system, of said quantity of interest.

2. Method according to claim 1, the step for staining the histological section prior to its digitization for generating said digital representation, also causing a distinctive staining of the erythrocytes, said method comprising, prior to the step for identifying the contours of the lumina of the hepatic vessels present in said digital representation, a step for distinguishing the pixels of said digital representation describing erythrocytes, and for modifying the respective values of said pixels by a value describing the void.

3. Method according to claim 1, for which the step of staining the histological section causing distinct staining of the hepatic tissue, the collagen, the void, and the cells forming bile ducts, consists of carrying out jointly, staining with picrosirius red and immunolabelling with CK19.

4. Method according to claim 2, for which the step of staining the histological section causing a distinct staining of the erythrocytes, consists of carrying out jointly, staining with light green SF.

5. Method according to claim 1, comprising a step for quantifying a quantity of interest describing a degree of steatosis of the hepatic tissue comprising:
identifying the contours of the lumina of the lipid macrovacuoles present in the digital representation;
adding the surface areas of said lipid macrovacuoles delimited by said contours and generating a total surface area (AM) of the lipid macrovacuoles identified within the digital representation;
normalizing said total surface area of lipid macrovacuoles by the surface area delimited by the largest of the determined contours characterizing the surface area of the entire section of the liver and thus generating the quantity of interest describing a degree of steatosis of said hepatic tissue;
causing an output, via the output human-machine interface of the system, of said quantity of interest.

6. Method according to claim 1, the step of staining the histological section prior to its digitization for generating said digital representation causing a distinctive staining of the active macrophages, said method comprising a step for quantifying a quantity of interest describing a degree of inflammation of the hepatic tissue, comprising:
identifying the contours of the lumina of the lipid macrovacuoles present in the digital representation;
distinguishing the pixels of said digital representation describing the active macrophages;
determining a number of crown-like structures constituted by active macrophages assembled around macrovacuoles in the hepatic tissue;
normalizing said number of crown-like structures per unit of surface area of the hepatic tissue of the histological section;
generating a quantity of interest describing a degree of inflammation of the hepatic tissue based on said number of crown-like structures, optionally normalized;
causing an output, via the output human-machine interface of the system, of said quantity of interest.

7. Method according to claim 6, for which the step of staining the histological section causing a distinctive staining of the macrophages, comprises carrying out an immunolabelling by glycoprotein F4/80, Mac-2 or CD68.

8. Method according to claim 1, the step of staining the histological section prior to its digitization for generating said digital representation, causing a distinctive staining of the hepatic cells in the process of degeneration, said method comprising a step for quantifying a quantity of interest describing a degree of inflammation of the hepatic tissue, comprising:
distinguishing the pixels of said digital representation describing the hepatic cells in the process of degeneration;
quantifying the area of the pixels of the digital representation describing hepatic cells in the process of degeneration;
normalizing said area by the total area of the hepatic tissue and obtaining a normalized area of the pixels of the digital representation describing hepatic cells in the process of degeneration;
generating a quantity of interest describing a degree of inflammation of the hepatic tissue based on said area of the pixels of the digital representation describing hepatic cells in the process of degeneration, optionally normalized;
causing an output, via the output human-machine interface of the system, of said quantity of interest.

9. Method according to claim 8, for which the step of staining the histological section causing a distinctive staining of the hepatic cells in the process of degeneration, comprises Sonic hedgehog immunolabelling combined with staining with hematoxylin.

10. Method according to claim 1, for which the step for quantifying a quantity of interest with reference to the hepatic tissue of the histological section (S) also comprises generating and recording, in the data memory, a score the integer value of which is representative of said quantity of interest.

11. A non-transitory computer-readable medium including program instructions, which when they are written to a program memory of a medical imaging system also including a processor, an output human-machine interface and a data memory, and interpreted or executed by said processor of the latter, cause the implementation of a method according to claim 1.

12. Medical imaging system including a processor, an output human-machine interface, a data memory, and a program memory, for which said program memory stores instructions of a non-transitory computer readable medium according to claim 11.

\* \* \* \* \*